United States Patent
Teramoto et al.

(10) Patent No.: US 10,899,701 B2
(45) Date of Patent: Jan. 26, 2021

(54) METHOD FOR PRODUCING N-(ALPHA-ALKOXYETHYL)FORMAMIDE

(71) Applicant: Mitsubishi Chemical Corporation, Chiyoda-ku (JP)

(72) Inventors: Kouji Teramoto, Tokyo (JP); Yasuharu Mori, Tokyo (JP); Hitoshi Nishimura, Tokyo (JP)

(73) Assignee: Mitsubishi Chemical Corporation, Chiyoda-ku (JP)

(*) Notice: Subject to any disclaimer, the term of this patent is extended or adjusted under 35 U.S.C. 154(b) by 0 days.

(21) Appl. No.: 16/242,032

(22) Filed: Jan. 8, 2019

(65) Prior Publication Data

US 2019/0135735 A1    May 9, 2019

Related U.S. Application Data

(63) Continuation of application No. PCT/JP2017/029197, filed on Aug. 10, 2017.

(30) Foreign Application Priority Data

Aug. 12, 2016 (JP) .................................. 2016-158645
Aug. 12, 2016 (JP) .................................. 2016-158646

(51) Int. Cl.
*C07C 231/12* (2006.01)
*C07C 231/08* (2006.01)
*C07C 233/18* (2006.01)
*C07C 23/24* (2006.01)
*C07C 231/24* (2006.01)

(52) U.S. Cl.
CPC .......... *C07C 231/12* (2013.01); *C07C 231/08* (2013.01); *C07C 231/24* (2013.01); *C07C 233/18* (2013.01)

(58) Field of Classification Search
CPC .................................................. C07C 233/18

USPC ........................................................ 564/215
See application file for complete search history.

(56) References Cited

U.S. PATENT DOCUMENTS

| | | | |
|---|---|---|---|
| 4,670,591 A | 6/1987 | Oftring et al. | |
| 5,574,185 A | 11/1996 | Sato et al. | |
| 6,342,199 B1 * | 1/2002 | Ellis | B01J 19/0013 423/659 |
| 2011/0294974 A1 | 12/2011 | Ohta et al. | |

FOREIGN PATENT DOCUMENTS

| | | |
|---|---|---|
| JP | 61-286357 | 12/1986 |
| JP | 6-179644 | 6/1994 |
| JP | 6-184071 | 7/1994 |
| JP | 6-298713 | 10/1994 |
| WO | WO 2010/079774 A1 | 7/2010 |

OTHER PUBLICATIONS

International Search Report dated Sep. 12, 2017 in PCT/JP2017/029197 filed Aug. 10, 2017 (with English Translation).
Extended European Search Report dated Jul. 5, 2019 in European Patent Application No. 17839597.6, 7 pages.

* cited by examiner

*Primary Examiner* — Ana Z Muresan
(74) *Attorney, Agent, or Firm* — Oblon, McClelland, Maier & Neustadt, L.L.P.

(57) ABSTRACT

Provided are a method for producing N-(α-alkoxyethyl)formamide, comprising adding an acid catalyst to the mixed liquid within 3 hours from start of mixing after mixing of N-(α-hydroxyethyl)formamide with an alcohol has been started, by which the N-(α-alkoxyethyl)formamide can be produced at a high yield without additional investment in plant and equipment while suppressing an increase in the temperature of the mixed liquid and preventing corrosion of a pipe; and a method for producing N-(α-alkoxyethyl)formamide, comprising degassing carbon dioxide in the reaction of N-(α-hydroxyethyl)formamide with an alcohol, by which the N-(α-alkoxyethyl)formamide having a decreased carbonate concentration can be produced.

7 Claims, 1 Drawing Sheet

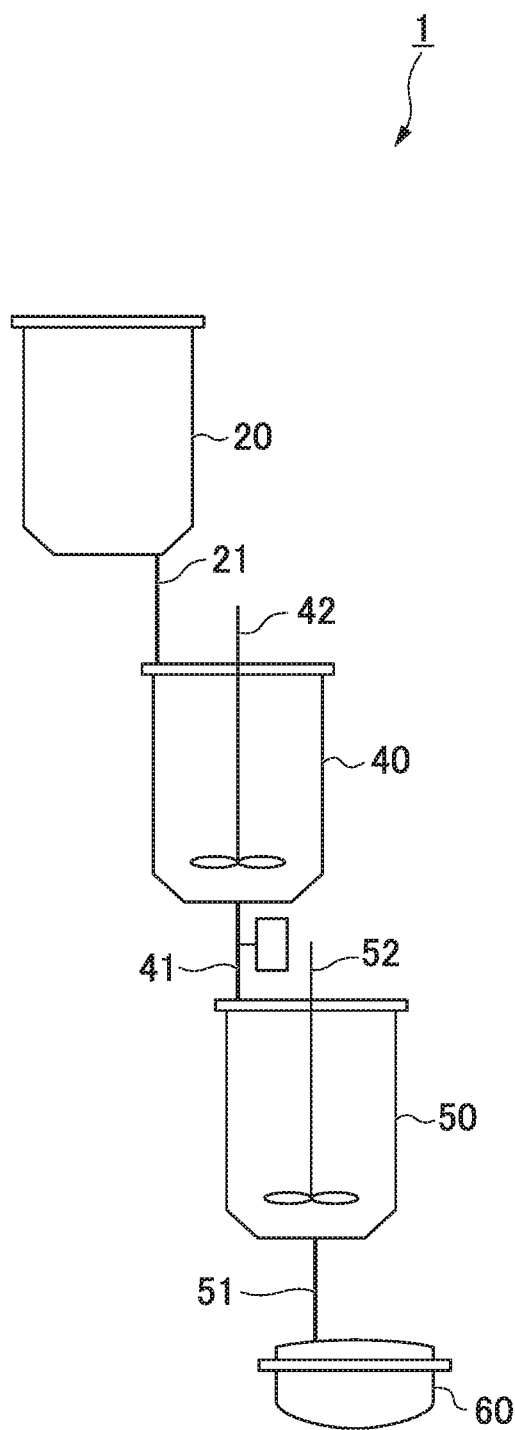

METHOD FOR PRODUCING N-(ALPHA-ALKOXYETHYL)FORMAMIDE

This application is a continuation application of International Application No. PCT/JP2017/029197, filed on Aug. 10, 2017, which claims the benefit of priority of the prior Japanese Patent Application No. 2016-158645 filed in Japan on Aug. 12, 2016 and the prior Japanese Patent Application No. 2016-158646 filed in Japan on Aug. 12, 2016, the entire contents of which are incorporated herein by reference.

TECHNICAL FIELD

The present invention relates to a method for producing a N-(α-alkoxyethyl)formamide.

BACKGROUND ART

N-(α-alkoxyethyl)formamides are an important substance as an intermediate material of N-vinylformamide.

N-(α-alkoxyethyl)formamides are obtained, for example, by reacting N-(α-hydroxyethyl)formamide, which is a reaction product of formamide with acetaldehyde, with an alcohol in the presence of an acid catalyst (see Patent Document 1).

N-(α-alkoxyethyl)formamides obtained are usually subjected to a purification treatment such as distillation to remove impurities therefrom.

CITATION LIST

Patent Document

Patent Document 1: JP 6-298713 A

SUMMARY OF THE INVENTION

Problem to be Solved by the Invention

However, in the conventional method for producing a N-(α-alkoxyethyl)formamide, the yield when N-(α-hydroxyethyl)formamide is reacted with an alcohol in the presence of an acid catalyst has not been necessarily satisfied.

As a result of intensive investigations, the present inventors have found out that the fact that N-(α-hydroxyethyl)formamide is unstable in an alcohol and is decomposed into formamide and acetaldehyde is a cause of a decrease in the yield when N-(α-hydroxyethyl)formamide is reacted with an alcohol in the presence of an acid catalyst.

It is only required to promptly react N-(α-hydroxyethyl)formamide with an alcohol in order to suppress the decomposition of N-(α-hydroxyethyl)formamide. In order to promptly conduct the reaction of N-(α-hydroxyethyl)formamide with an alcohol, it is only required to simultaneously add an alcohol and an acid catalyst to N-(α-hydroxyethyl)formamide or to dissolve an acid catalyst in an alcohol in advance and to add this alcohol solution of an acid catalyst to N-(α-hydroxyethyl)formamide.

However, in the method in which an alcohol and an acid catalyst are simultaneously added to N-(α-hydroxyethyl)formamide, the temperature of the mixed solution rapidly increases and thus a side reaction is promoted by this.

On the other hand, in the method in which an alcohol solution of an acid catalyst is added to N-(α-hydroxyethyl)formamide, investment in plant and equipment is required to newly provide a tank for preparing the alcohol solution of an acid catalyst. In addition, in a case in which an alcohol solution of an acid catalyst is prepared by mixing an alcohol with an acid catalyst in a pipe, there is a problem that a rapid heat generation takes place in the mixed portion of the alcohol with the acid catalyst and the pipe is likely to corrode.

In this manner, new problems such as an increase in the temperature of the mixed solution, additional investment in plant and equipment, and corrosion of the pipe occur in the simultaneous addition of an alcohol and an acid catalyst to N-(α-hydroxyethyl)formamide and the addition of an alcohol solution of an acid catalyst to N-(α-hydroxyethyl)formamide.

An aspect of the invention has been made in view of the above circumstances, and an object thereof is to provide a method for producing a N-(α-alkoxyethyl)formamide, by which a N-(α-alkoxyethyl)formamide can be produced at a high yield without additional investment in plant and equipment while suppressing an increase in the temperature of a mixed solution and preventing corrosion of a pipe.

In addition, in the conventional method for producing a N-(α-alkoxyethyl)formamide, there is a case in which the viscosity (hereinafter, also simply referred to as the "column bottom liquid viscosity") of the column bottom liquid at the bottom portion of the distillation column increases when a N-(α-alkoxyethyl)formamide obtained is purified through distillation. When the column bottom liquid viscosity increases, it is difficult to draw out the column bottom liquid from the bottom portion of the distillation column and this hinders the distillation operation in some cases.

As a result of intensive investigations, the inventors have found out that the fact that the carbonate used in the reaction of formamide with acetaldehyde remains in the N-(α-alkoxyethyl)formamide is a cause of an increase in the column bottom liquid viscosity.

An aspect of the invention has been made in view of the above circumstances, and an object thereof is to provide a method for producing a N-(α-alkoxyethyl)formamide, by which a N-(α-alkoxyethyl)formamide having a decreased carbonate concentration can be produced.

Means for Solving Problems

[1] A method for producing N-(α-alkoxyethyl)formamide, including:

producing N-(α-hydroxyethyl)formamide by mixing formamide with acetaldehyde in presence of a carbonate and precipitating N-(α-hydroxyethyl)formamide; and producing the N-(α-alkoxyethyl)formamide by mixing the N-(α-hydroxyethyl)formamide with an alcohol, in which the production of the N-(α-alkoxyethyl)formamide is conducted in presence of an acid catalyst, and the acid catalyst is added to a mixed liquid containing the N-(α-hydroxyethyl)formamide and the alcohol within 3 hours from start of mixing after mixing of the N-(α-hydroxyethyl)formamide with the alcohol has been started in the production of the N-(α-alkoxyethyl)formamide.

[2] The method for producing N-(α-alkoxyethyl)formamide according to [1], in which the acid catalyst is added to the mixed liquid containing the N-(α-hydroxyethyl)formamide and the alcohol after 1 minute or more and within 3 hours from start of mixing after mixing of the N-(α-hydroxyethyl)formamide with the alcohol has been started in the production of the N-(α-alkoxyethyl)formamide.

[3] The method for producing N-(α-alkoxyethyl)formamide according to [1] or [2], in which a temperature of the mixed liquid containing the N-(α-hydroxyethyl)formamide and the alcohol immediately before addition of the acid catalyst is 30° C. or less.

[4] The method for producing N-(α-alkoxyethyl)formamide according to [3], in which a temperature of the mixed liquid containing the N-(α-hydroxyethyl)formamide and the alcohol immediately before addition of the acid catalyst is 10° C. or less.

[5] A method for producing N-(α-alkoxyethyl)formamide, including:
producing N-(α-hydroxyethyl)formamide by mixing formamide with acetaldehyde in presence of a carbonate and precipitating N-(α-hydroxyethyl)formamide; and
producing the N-(α-alkoxyethyl)formamide by mixing the N-(α-hydroxyethyl)formamide with an alcohol, in which
the production of the N-(α-alkoxyethyl)formamide is conducted in presence of an acid catalyst, and
carbon dioxide in a reaction liquid is degassed in the production of the N-(α-alkoxyethyl)formamide.

[6] A method for producing N-(α-alkoxyethyl)formamide, including:
producing N-(α-hydroxyethyl)formamide by mixing formamide with acetaldehyde in presence of a carbonate and precipitating N-(α-hydroxyethyl)formamide; and
producing the N-(α-alkoxyethyl)formamide by mixing the N-(α-hydroxyethyl)formamide with an alcohol, in which
the production of the N-(α-alkoxyethyl)formamide is conducted in presence of an acid catalyst, and
a carbonate ion concentration in a solution that is obtained by neutralizing a reaction mixture obtained in the production of the N-(α-alkoxyethyl)formamide with a base and subjecting the reaction mixture neutralized to solid-liquid separation and contains the N-(α-alkoxyethyl)formamide is 500 ppm or less.

[7] The method for producing N-(α-alkoxyethyl)formamide according to [5], in which the degassing of carbon dioxide is conducted by blowing of an inert gas into the reaction liquid.

[8] The method for producing N-(α-alkoxyethyl)formamide according to [7], in which a linear velocity of the inert gas in the blowing of an inert gas is from 0.1 to 20 m/hr.

[9] The method for producing N-(α-alkoxyethyl)formamide according to [7] or [8], in which the blowing of an inert gas is conducted when the reaction liquid is under an acidic condition.

[10] The method for producing N-(α-alkoxyethyl)formamide according to [1], in which carbon dioxide in a reaction liquid is degassed in the production of the N-(α-alkoxyethyl)formamide.

[11] The method for producing N-(α-alkoxyethyl)formamide according to [1], in which a carbonate ion concentration in a solution that is obtained by neutralizing a reaction mixture obtained in the production of the N-(α-alkoxyethyl)formamide with a base and subjecting the reaction mixture neutralized to solid-liquid separation and contains the N-(α-alkoxyethyl)formamide is 500 ppm or less.

[12] The method for producing N-(α-alkoxyethyl)formamide according to [10], in which the degassing of carbon dioxide is conducted by blowing of an inert gas into the reaction liquid.

[13] The method for producing N-(α-alkoxyethyl)formamide according to [12], in which a linear velocity of the inert gas in the blowing of an inert gas is from 0.1 to 20 m/hr.

[14] The method for producing N-(α-alkoxyethyl)formamide according to [12] or [13], in which the blowing of an inert gas is conducted when the reaction liquid is under an acidic condition.

Effect of the Invention

According to some aspects of the method for producing a N-(α-alkoxyethyl)formamide of the invention, it is possible to produce a N-(α-alkoxyethyl)formamide at a high yield without additional investment in plant and equipment while suppressing an increase in the temperature of a mixed solution and preventing corrosion of a pipe.

In addition, according to some aspects of the method for producing a N-(α-alkoxyethyl)formamide of the invention, it is possible to produce a N-(α-alkoxyethyl)formamide having a decreased carbonate concentration.

BRIEF DESCRIPTION OF DRAWINGS

FIG. 1 is a schematic configuration diagram illustrating a production apparatus of a N-(α-alkoxyethyl)formamide used in Examples and Comparative Examples.

MODE(S) FOR CARRYING OUT THE INVENTION

The method for producing a N-(α-alkoxyethyl)formamide of the invention includes the following step (1) and step (2).

Step (1):
a step of producing N-(α-hydroxyethyl)formamide by mixing formamide with acetaldehyde in the presence of a carbonate and precipitating N-(α-hydroxyethyl)formamide.

Step (2):
a step of producing a N-(α-alkoxyethyl)formamide by mixing the N-(α-hydroxyethyl)formamide obtained in the step (1) with an alcohol.

Moreover, the step (2) is carried out in the presence of an acid catalyst.

Hereinafter, the respective steps will be described in detail.

The step (1) is a step (hereinafter, also referred to as the "hydroxylation step") of producing N-(α-hydroxyethyl)formamide by mixing formamide with acetaldehyde in the presence of a carbonate and precipitating N-(α-hydroxyethyl)formamide.

The molar ratio (formamide:acetaldehyde) of formamide to acetaldehyde to be used in the hydroxylation step is preferably from 1:1 to 1:10 and more preferably from 1:1 to 1:5.

The conversion of formamide can be increased by setting the molar ratio of acetaldehyde to be excessive.

Examples of the carbonate to be used in the hydroxylation step may include a carbonate of an alkali metal, and specific examples thereof may include sodium carbonate, sodium hydrogencarbonate, potassium carbonate, potassium hydrogencarbonate, lithium carbonate, and lithium hydrogencarbonate.

Among these, potassium hydrogencarbonate is preferable from the viewpoint of, for example, decreasing by-products such as an aldol condensate of acetaldehyde to be generated when formamide reacts with acetaldehyde.

The amount of the carbonate to be used is preferably from 0.01 to 10 mol % and more preferably from 0.1 to 2 mol % with respect to the molar number (100 mol %) of formamide to be used.

Formamide sufficiently reacts with acetaldehyde when the amount of the carbonate to be used is equal to or more than the lower limit value, and excessive remaining of the carbonate can be suppressed when the amount of the carbonate to be used is equal to or less than the upper limit value.

Specific examples of the solvent to be used in the hydroxylation step may include aliphatic hydrocarbons such as hexane, heptane, and cyclohexane; aromatic hydrocarbons such as benzene, toluene, and xylene; and halogenated hydrocarbons such as methylene chloride and chloroform.

These solvents are preferable from the viewpoint of easily precipitating N-(α-hydroxyethyl)formamide to be obtained.

The amount of the solvent to be used is preferably from 0.2 to 10 parts by mass with respect to the mass (1 part by mass) of formamide to be used.

The reaction temperature in the hydroxylation step is not particularly limited, and it is usually about from −10° C. to 100° C. The reaction temperature is preferably from 0° C. to 40° C. from the viewpoint of the reaction yield in the present step and precipitation of N-(α-hydroxyethyl)formamide generated. It is possible to improve the reaction yield by precipitating N-(α-hydroxyethyl)formamide and removing the N-(α-hydroxyethyl)formamide out of the reaction system.

The reaction temperature in the hydroxylation step can be measured by using a thermometer to be usually used industrially such as a thermocouple thermometer.

A specific aspect of the hydroxylation step is not particularly limited, but a mixed solution of acetaldehyde with a solvent is used as a base solution and formamide in which a carbonate is dissolved is added thereto dropwise.

Furthermore, a method in which N-(α-hydroxyethyl)formamide of a product is precipitated after the reaction or in the middle of the reaction and preferably a method in which N-(α-hydroxyethyl)formamide is precipitated as a crystal are general. In order to smoothly conduct this precipitation, an operation to add a small amount of N-(α-hydroxyethyl)formamide crystals as a seed crystal may be conducted before the dropwise addition of formamide in which a carbonate is dissolved is completed.

As the amount of the seed crystal to be used in this case, the amount of seed crystals to be used in a usual crystallization operation can be adopted.

By precipitating N-(α-hydroxyethyl)formamide, the precipitate can be subjected to the next step only by taking out the precipitate by a method such as filtration and most of the solvent can be separated and recovered. In addition, a method in which the solvent is not separated and recovered from the mixture obtained in the hydroxylation step but the mixture is subjected to the next step as it is can also be adopted.

The mixture obtained in the hydroxylation step contains unreacted formamide and acetaldehyde, an aldol condensate of acetaldehyde which is a by-product, the carbonate, the solvent, and the like in addition to N-(α-hydroxyethyl)formamide which is the objective product of the hydroxylation step.

The step (2) is a step (hereinafter also referred to as the "alkoxylation step") of producing a N-(α-alkoxyethyl)formamide by mixing the N-(α-hydroxyethyl)formamide obtained in the step (1) with an alcohol.

The present step is carried out in the presence of an acid catalyst.

As the N-(α-hydroxyethyl)formamide obtained in the hydroxylation step, the mixture obtained in the hydroxylation step may be used or N-(α-hydroxyethyl)formamide may be isolated from the mixture obtained in the hydroxylation step and used.

In the alkoxylation step, a primary or secondary alcohol is used as the alcohol.

From the viewpoint of the reactivity in the alkoxylation step and the handling properties of a N-(α-alkoxyethyl) formamide to be generated, an alcohol having from 1 to 8 carbon atoms is preferable and an alcohol having from 1 to 4 carbon atoms is more preferable.

Specific examples of the alcohol to be used in the alkoxylation step may include methanol, ethanol, n-propanol, n-butanol, isobutyl alcohol, n-pentanol, n-hexanol, n-heptanol, n-octanol, benzyl alcohol, 2-methoxyethanol, 2-ethoxyethanol, 2-propoxyethanol, 2-butoxyethanol, diethylene glycol monomethyl ether, ethylene glycol, propylene glycol, 1,4-butanediol, and diethylene glycol.

Among these, a primary alcohol is preferable and methanol is particularly preferable since the boiling points of the raw material and product are low.

In the alkoxylation step, it is preferable to use the alcohol in an excess amount in order to increase the yield of the product, and specifically, the molar number of the alcohol is preferably from 1.1 to 50 times and more preferably from 2.0 to 30 times the molar number of N-(α-hydroxyethyl)formamide to be used.

Incidentally, the alcohol in the alkoxylation step is also used as a solvent by being used in an excess amount.

Examples of the acid catalyst to be used in the alkoxylation step may include a mineral acid, an organic acid, an ion exchange resin exhibiting weak acidity or strong acidity, and a solid acid catalyst.

Among these, a strongly acidic catalyst is preferable, and specific examples thereof may include sulfuric acid, hydrochloric acid, nitric acid, sulfamic acid, methanesulfonic acid, and crosslinked polystyrene sulfonic acid.

As the amount of the acid catalyst to be used in the alkoxylation step, the total amount of the amount required to neutralize the carbonate which has been used in the hydroxylation step and contained in the N-(α-hydroxyethyl)formamide and the amount required to conduct the reaction in the alkoxylation step is required. As the total amount of these, the amount of the acid catalyst to be used in the alkoxylation step is preferably from 0.001 to 10 mol % and more preferably from 0.1 to 5 mol % with respect to the molar number (100 mol %) of N-(α-hydroxyethyl)formamide.

The temperature of the mixed solution after N-(α-hydroxyethyl)formamide, the alcohol, and the acid catalyst are mixed together is not particularly limited, but it is preferably from −10° C. to 60° C., more preferably from 0° C. to 40° C., and still more preferably from 5° C. to 30° C. from the viewpoint of the reactivity in the alkoxylation step and the stability of N-(α-hydroxyethyl)formamide.

After completion of the alkoxylation step, usually, the acid catalyst is neutralized with an alkali compound or the acid catalyst is filtered and separated in the case of being in a solid state such as an ion exchange resin.

Incidentally, particularly in the production method of the invention adopting the first aspect of the alkoxylation step to be described later, the neutralization treatment itself after completion of the alkoxylation step is not an essential operation, but it is preferable to conduct the neutralization treatment after completion of the alkoxylation step from the viewpoint of minimizing the decomposition of the N-(α-alkoxyethyl)formamide in the step of purifying and recovering the N-(α-alkoxyethyl)formamide since the N-(α-alkoxyethyl)formamide which is the product is more stable under a neutral condition.

In the alkoxylation step, there is a case in which the carbonate is contained in the N-(α-hydroxyethyl)formamide to be used in the alkoxylation step, for example, in the case of using the mixture obtained in the hydroxylation step as N-(α-hydroxyethyl)formamide. Sulfuric acid reacts with the carbonate to generate a sulfate such as sodium sulfate or potassium sulfate, for example, when sulfuric acid is used as an acid catalyst in the alkoxylation step at that time. These sulfates are hardly dissolved in the mixture after completion of the reaction in the alkoxylation step, and these sulfates can be thus separated from the N-(α-alkoxyethyl)formamide, which is the objective product in the alkoxylation step, for example, by using means such as solid-liquid separation, preferably by solid-liquid separation using a filter and the like.

Impurities and the like can be removed from the solution, which is separated by solid-liquid separation and contains a N-(α-alkoxyethyl)formamide, by purification through distillation.

In the production method of the invention, the acid catalyst can be added to the mixture containing N-(α-hydroxyethyl)formamide and the alcohol within 3 hours from the start of mixing after mixing of N-(α-hydroxyethyl) formamide with the alcohol has been started in the alkoxylation step.

Hereinafter, in the alkoxylation step of the method for producing a N-(α-alkoxyethyl)formamide of the invention, an aspect including adding the acid catalyst to the mixture containing N-(α-hydroxyethyl)formamide and the alcohol within 3 hours from the start of mixing after mixing of N-(α-hydroxyethyl)formamide with the alcohol has been started is referred to as the first aspect of the alkoxylation step.

The specific procedure of the first aspect of the alkoxylation step is as follows.

First, N-(α-hydroxyethyl)formamide and an alcohol are mixed to obtain a mixed solution containing the N-(α-hydroxyethyl)formamide and the alcohol.

Subsequently, an acid catalyst is added to the mixed solution containing N-(α-hydroxyethyl)formamide and the alcohol. At this time, the acid catalyst is added to the mixed solution within 3 hours from the start of mixing after mixing of N-(α-hydroxyethyl)formamide with the alcohol has been started.

It is preferable that the addition of the acid catalyst to the mixed solution is conducted after 10% or more, preferably 30% or more, more preferably 50% or more, still more preferably 80% or more, and most preferably 100% of the entire alcohol to be mixed with N-(α-hydroxyethyl)formamide has been mixed.

The addition of the acid catalyst is conducted preferably after a lapse of 1 minute or more and more preferably after a lapse of 5 minutes or more and within 3 hours, preferably within 2 hours, and more preferably within 1 hour from the start of mixing after mixing of N-(α-hydroxyethyl)formamide with the alcohol has been started.

As a preferred aspect among these, the addition of the acid catalyst is started after a lapse of 1 minute or more and more preferably after a lapse of 5 minutes or more from the start of mixing after mixing of N-(α-hydroxyethyl)formamide with the alcohol has been started, and the addition of the acid catalyst is completed within 3 hours, preferably within 2 hours, and more preferably within 1 hour from the start of mixing.

As the time from the start of mixing to the addition of the acid catalyst to the mixed solution is within the above range after mixing of N-(α-hydroxyethyl)formamide with the alcohol has been started, it is possible to suppress the decomposition of N-(α-hydroxyethyl)formamide in the alcohol and to increase the reaction yield in the alkoxylation step. Moreover, it is also possible to suppress a rapid increase in the temperature of the mixed solution since the acid catalyst is added after N-(α-hydroxyethyl)formamide is mixed with the alcohol.

In the invention, a particularly remarkable effect can be obtained when a N-(α-alkoxyethyl)formamide is industrially produced on a large scale, for example, a volume of the reaction mixture or reaction tank of 100 L, preferably 200 L, and more preferably 500 L or more.

In the first aspect of the alkoxylation step, the temperature of the mixed solution immediately before the addition of the acid catalyst is preferably 30° C. or less, more preferably 20° C. or less, and still more preferably 10° C. or less. It is possible to suppress the decomposition of N-(α-hydroxyethyl)formamide in the alcohol until the acid catalyst is added to the mixed solution when the temperature of the mixed solution immediately before the addition of the acid catalyst is equal to or less than the upper limit value.

In addition, the temperature of the mixed solution immediately before the addition of the acid catalyst may be low as long as the mixed solution does not freeze, but it is preferably −20° C. or more, more preferably −15° C. or more, and still more preferably −5° C. or more so that the reaction temperature after the addition of the acid catalyst to the mixed solution is not too low.

For example, in the first aspect of the alkoxylation step, the temperature of the mixed solution immediately before the addition of the acid catalyst is preferably from −20° C. to 30° C., more preferably from −15° C. to 20° C., and still more preferably from −5° C. to 10° C.

According to the production method of the invention adopting the first aspect of the alkoxylation step, it is possible to obtain the following effects (1) to (4).

(1) In the alkoxylation step, it is not required to newly provide a tank for preparing the alcohol solution of an acid catalyst described above and the investment in plant and equipment for the tank is also not required by separately adding the alcohol and the acid catalyst with a time lag.

(2) It is possible to prevent heat generation at the mixed portion of the alcohol with the acid catalyst and corrosion of the pipe since it is not required to prepare an alcohol solution of an acid catalyst by mixing the alcohol with the acid catalyst in the pipe.

(3) According to the production method of the invention, the reaction yield of the alkoxylation step increases since the acid catalyst is added within 3 hours from the start of mixing after mixing of N-(α-hydroxyethyl)formamide with the alcohol has been started.

The reason for this is considered as follows.

As described above, N-(α-hydroxyethyl)formamide is unstable in an alcohol and is thus decomposed into formamide and acetaldehyde. The alkoxylation step is carried out while substantially suppressing the decomposition of N-(α-hydroxyethyl)formamide by adding the acid catalyst within 3 hours after the addition of the alcohol. As a result, it is considered that the reaction yield of the alkoxylation step increases.

(4) It is also possible to suppress a rapid increase in the temperature of the mixed solution since the acid catalyst is added to N-(α-hydroxyethyl)formamide after the alcohol has been added to N-(α-hydroxyethyl)formamide.

The reason for this is considered as follows.

The temperature of the mixed solution rapidly increases particularly locally in the case of simultaneously adding the alcohol and the acid catalyst to N-(α-hydroxyethyl)formamide. On the other hand, N-(α-hydroxyethyl)formamide is diluted with a large amount of alcohol in the case of adding the acid catalyst to N-(α-hydroxyethyl)formamide after the alcohol has been added to N-(α-hydroxyethyl)formamide. It is considered that an increase in the temperature of the mixed solution is suppressed since the acid catalyst is added to a large amount of alcohol in such a diluted state.

Moreover, it is considered that an increase in the temperature of the mixed solution is further suppressed since the endothermic reaction when N-(α-hydroxyethyl)formamide is dissolved in the alcohol compensates the heat generation when the acid catalyst is added.

In this manner, according to the production method of the invention adopting the first aspect of the alkoxylation step, it is possible to produce a N-(α-alkoxyethyl)formamide at a high yield without additional investment in plant and equipment for the tank while suppressing an increase in the temperature of the mixed solution and preventing corrosion of the pipe.

In the production method of the invention, it is possible to conduct degassing of carbon dioxide in the alkoxylation step.

Hereinafter, in the alkoxylation step of the method for producing a N-(α-alkoxyethyl)formamide of the invention, an aspect including conducting degassing of carbon dioxide in a reaction solution is referred to as the second aspect of the alkoxylation step.

In the alkoxylation step of the method for producing a N-(α-alkoxyethyl)formamide of the invention, the second aspect of the alkoxylation step may be adopted together with the first aspect of the alkoxylation step described above or the second aspect of the alkoxylation step may be adopted without adopting the first aspect of the alkoxylation step.

Incidentally, in the present specification, an aspect in which the second aspect of the alkoxylation step is adopted as well as the first aspect of the alkoxylation step is adopted is referred to as the second aspect of the alkoxylation step.

In the second aspect of the alkoxylation step, an aspect corresponding to the first aspect of the alkoxylation step described above can be adopted except degassing of carbon dioxide.

In the alkoxylation step of the method for producing a N-(α-alkoxyethyl)formamide of the invention, it is possible to produce a N-(α-alkoxyethyl)formamide having a decreased carbonate concentration by adopting the second aspect of the alkoxylation step.

In the alkoxylation step of the method for producing a N-(α-alkoxyethyl)formamide of the invention, the method for adding the acid catalyst in the alkoxylation step is not particularly limited, but for example, the acid catalyst may be added to the mixed solution of N-(α-hydroxyethyl)formamide with the alcohol in a case in which the first aspect of the alkoxylation step is not adopted but degassing of carbon dioxide is conducted in the alkoxylation step. In addition, an alcohol solution of an acid catalyst may be prepared by dissolving the acid catalyst in the alcohol in advance and the alcohol solution of an acid catalyst prepared may be added to N-(α-hydroxyethyl)formamide.

In the alkoxylation step, there is a case in which a carbonate is contained in the N-(α-hydroxyethyl)formamide to be used in the alkoxylation step, for example, in the case of using the mixture obtained in the hydroxylation step as N-(α-hydroxyethyl)formamide. The carbonate is converted into a carbonate ion and carbon dioxide under a condition exhibiting stronger acidity than carbonic acid. Hence, the pH of the mixed solution in the alkoxylation step is acidic and a carbonate ion and carbon dioxide derived from the carbonate are generated since an acid catalyst exhibiting stronger acidity than carbonic acid is used in the alkoxylation step.

After completion of the alkoxylation step, a neutralization operation using a base is conducted in order to maintain the stability of the N-(α-alkoxyethyl)formamide. The carbonate ion reforms the carbonate and the carbonate is contained in the N-(α-alkoxyethyl)formamide when carbon dioxide remains in this neutralization operation.

It is considered that this carbonate causes an increase in the column bottom liquid viscosity when purifying the N-(α-alkoxyethyl)formamide through distillation. Hence, in order to suppress an increase in the column bottom liquid viscosity at the time of purification through distillation, it is preferable to suppress reformation of the carbonate by removing carbon dioxide in the reaction system in the alkoxylation step.

In the second aspect of the alkoxylation step, carbon dioxide in the reaction solution is degassed and the carbon dioxide is forcibly removed out of the reaction system in the alkoxylation step.

In the present aspect, it is only required that the reaction solution contains at least N-(α-hydroxyethyl)formamide. This is because carbon dioxide, which is a target of degassing, is derived from the carbonate accompanying N-(α-hydroxyethyl)formamide in some cases. The reaction solution contains not only N-(α-hydroxyethyl)formamide and the alcohol, which are the reactants, but also components such as a reaction product, a catalyst component, and impurities derived from raw materials other than N-(α-hydroxyethyl)formamide and the alcohol.

In addition, components other than carbon dioxide may be degassed when degassing carbon dioxide from the reaction solution.

Reformation of the carbonate is suppressed by conducting degassing of carbon dioxide in the alkoxylation step. As a result, N-(α-alkoxyethyl)formamide having a decreased carbonate concentration is obtained and an increase in the column bottom liquid viscosity hardly occurs even when a N-(α-alkoxyethyl)formamide to be obtained by adopting the second aspect of the alkoxylation step is purified through distillation.

The concentration of carbonate ion in the solution which is obtained by neutralizing the reaction mixture obtained by the alkoxylation step with a base and subjecting the reaction mixture neutralized to solid-liquid separation and contains a N-(α-alkoxyethyl)formamide is preferably 500 ppm or less and more preferably 400 ppm or less.

The concentration of carbonate ion in the solution containing a N-(α-alkoxyethyl)formamide is expressed by the concentration of carbonate ion to be obtained by a commonly used method for measuring the concentration of carbonate ion such as ion chromatography or titration.

The base to be used in the neutralization of the reaction mixture obtained by the alkoxylation step is preferably a strong base, specific examples thereof may include sodium hydroxide, potassium hydroxide, lithium hydroxide, and calcium hydroxide, and sodium hydroxide is preferable among these.

The base to be used in the neutralization may be used singly, or two or more kinds thereof may be used concurrently.

The neutralization of the reaction mixture obtained by the alkoxylation step can be conducted by adding a base to the reaction mixture obtained by the alkoxylation step until the concentration of hydrogen ion (pH) in the reaction mixture reaches from 5 to 9.

For solid-liquid separation of the neutralized reaction mixture, commonly used solid-liquid separation means can be used, but examples thereof may include a metal filter type pressure filter and a centrifuge.

The method for degassing carbon dioxide in the second aspect of the alkoxylation step is not particularly limited as long as it is a method by which carbon dioxide in the reaction solution can be degassed and removed out of the reaction system, but it is preferable to conduct degassing of carbon dioxide by blowing of an inert gas into the reaction solution.

Examples of the inert gas may include nitrogen, argon, helium, neon, krypton, xenon, and radon.

The linear velocity of the inert gas in the blowing of an inert gas also depends on the type of reaction tank and the stirring strength, but it is generally preferably from 0.1 to 20 m/hr, more preferably from 0.5 to 10 m/hr, still more preferably from 1 to 5 m/hr, and particularly preferably from 2 to 4 m/hr. In addition, the linear velocity is preferably from 1 to 20 m/hr and more preferably from 2 to 20 m/hr as another aspect and it is preferably from 1 to 10 m/hr and more preferably from 2 to 10 m/hr as still another aspect.

When the linear velocity of the inert gas in the blowing of an inert gas is equal to or more than the lower limit value, it is possible to sufficiently remove carbon dioxide and to obtain a N-(α-alkoxyethyl)formamide in which the carbonate concentration is sufficiently decreased. Carbon dioxide is more likely to be removed as the linear velocity of the inert gas in the blowing of an inert gas is higher, but the effect of removing carbon dioxide hardly changes even when the linear velocity of the inert gas in the blowing of an inert gas exceeds the upper limit value. From the viewpoint of the balance between the effect of removing carbon dioxide and the production cost, the linear velocity of the inert gas in the blowing of an inert gas is preferably equal to or less than the upper limit value.

Degassing of carbon dioxide in the second aspect of the alkoxylation step is preferably conducted when the reaction solution is under an acidic condition. As the acidic condition, a pH of from 1 to 5 is preferable and a pH of from 1 to 3 is more preferable.

Degassing of carbon dioxide in the second aspect of the alkoxylation step may be conducted after the alcohol and the acid catalyst have been added to N-(α-hydroxyethyl)formamide or before the alcohol is added to N-(α-hydroxyethyl)formamide.

However, it is required to conduct degassing of carbon dioxide under an acidic condition since a carbonate ion and carbon dioxide are generated under an acidic condition as described above. For this reason, degassing of carbon dioxide is conducted after addition of the acid catalyst to N-(α-hydroxyethyl)formamide has been started and preferably after addition of the acid catalyst has been completed and before the neutralization after the alkoxylation step is completed and preferably before the neutralization is started.

In addition, N-(α-hydroxyethyl)formamide is usually obtained in a solid state and it is thus preferable to conduct degassing of carbon dioxide in a state in which N-(α-hydroxyethyl)formamide is dissolved in the alcohol when the efficiency of degassing of carbon dioxide and the stability of N-(α-hydroxyethyl)formamide are taken into consideration. In other words, it is preferable to conduct degassing of carbon dioxide during the time from the completion of the addition of the alcohol and the acid catalyst to N-(α-hydroxyethyl)formamide to the start of the neutralization after the alkoxylation step.

The temperature for degassing of carbon dioxide in the second aspect of the alkoxylation step is not particularly limited, but it is preferably from −20° C. to 30° C., more preferably from −10° C. to 25° C., and still more preferably from 0° C. to 20° C. In addition, the temperature is preferably from −10° C. to 60° C., more preferably from 0° C. to 40° C., and still more preferably from 5° C. to 30° C. as another aspect.

The time for degassing of carbon dioxide in the second aspect of the alkoxylation step also depends on the linear velocity of the inert gas, but it is not particularly limited as long as carbon dioxide is sufficiently removed, and it is preferably from 1 to 600 minutes and more preferably from 5 to 300 minutes.

According to the production method of the invention adopting the second aspect of the alkoxylation step, remaining of the carbonate used in the hydroxylation step in the N-(α-alkoxyethyl)formamide is suppressed and a N-(α-alkoxyethyl)formamide having a decreased carbonate concentration is obtained since degassing of carbon dioxide is conducted in the alkoxylation step.

For this reason, an increase in the column bottom liquid viscosity hardly occurs even when a N-(α-alkoxyethyl)formamide to be obtained is purified through distillation.

The reason for this is considered as follows.

As described above, it is considered that the fact that the carbonate to be used in the hydroxylation step remains in the N-(α-alkoxyethyl)formamide is a cause of an increase in the column bottom liquid viscosity. The carbonate remaining is converted into a carbonate ion and carbon dioxide under a condition exhibiting stronger acidity than carbonic acid. In a case in which carbon dioxide is not sufficiently removed, the carbonate ion reforms the carbonate at the time of neutralization after completion of the alkoxylation step and these carbonates cannot be easily separated through filtration and the like and are thus contained in the N-(α-alkoxyethyl)formamide as a carbonate.

On the other hand, a decomposition product of the carbonate remaining can be removed as gaseous carbon dioxide under an acidic condition. Hence, it is possible to remove the decomposition product of the carbonate remaining out of the reaction system as gaseous carbon dioxide and to sufficiently remove carbon dioxide from the N-(α-alkoxyethyl)formamide when degassing of carbon dioxide is conducted in the alkoxylation step, and reformation of the carbonate is thus suppressed.

In this manner, according to the production method of the invention adopting the second aspect of the alkoxylation step, it is possible to produce a N-(α-alkoxyethyl)formamide in which the carbonate concentration is sufficiently decreased and it is thus considered that an increase in the column bottom liquid viscosity hardly occurs even when a N-(α-alkoxyethyl)formamide to be obtained is purified through distillation.

EXAMPLES

Hereinafter, the invention will be more specifically described with reference to Examples, but the invention is not limited thereto.

Incidentally, "%" represents "% by mass" unless otherwise stated.

Example A1

By using the production apparatus illustrated in FIG. 1, N-(α-hydroxyethyl)formamide was produced and N-(α-methoxyethyl)formamide of a N-(α-alkoxyethyl)formamide was subsequently produced as follows.

The production apparatus illustrated in FIG. 1 includes a catalyst dissolving tank 20 for storing a formamide solution of a carbonate which is a basic catalyst, a hydroxylation reaction tank 40 which is provided below the catalyst dissolving tank 20 and is for mixing formamide with acetaldehyde and producing N-(α-hydroxyethyl)formamide, an alkoxylation reaction tank 50 which is provided below the hydroxylation reaction tank 40 and is for mixing N-(α-hydroxyethyl)formamide produced in the hydroxylation reaction tank 40 with an alcohol and producing a N-(α-alkoxyethyl)formamide, and a filter 60 provided below the alkoxylation reaction tank 50.

The catalyst dissolving tank 20 and the hydroxylation reaction tank 40 are connected to each other by a first supply pipe 21.

The hydroxylation reaction tank 40 and the alkoxylation reaction tank 50 are connected to each other by a second supply pipe 41.

The alkoxylation reaction tank 50 and the filter 60 are connected to each other by a third supply pipe 51.

<Production of N-(α-hydroxyethyl)formamide>

In the catalyst dissolving tank 20, 1.69 kg of potassium hydrogencarbonate as a carbonate and 95.2 kg of formamide were put, and a formamide solution of potassium hydrogencarbonate was prepared.

Separately, 384 kg of industrial toluene was charged in the hydroxylation reaction tank 40 which was made of glass lining and equipped with a stirrer 42 and a temperature controller (not illustrated), degassing was conducted using nitrogen gas, 107 kg of acetaldehyde was added to the toluene, a toluene solution of acetaldehyde was thus prepared, and the temperature of the solution was adjusted to 20° C.

Subsequently, 20% amount of the formamide solution of potassium hydrogencarbonate in the catalyst dissolving tank 20 was added to the toluene solution of acetaldehyde in the hydroxylation reaction tank 40 over 15 minutes. Thereafter, the remaining amount of the formamide solution of potassium hydrogencarbonate was further added to the mixed solution over 3 hours, and the resultant mixed solution was stirred for 1 hour, thereby obtaining a slurry-like mixture in which a solid was precipitated.

The slurry-like mixture obtained was transferred to the alkoxylation reaction tank 50 which was made of a glass lining and equipped with a stirrer 52 and a temperature controller (not illustrated), and toluene of the solvent was removed therefrom through filtration.

A part of the solid component mixture filtered was collected and analyzed by liquid chromatography under the following conditions, and as a result, the solid component mixture contained N-(α-hydroxyethyl)formamide at 64.3%, formamide at 0.7%, acetaldehyde at 1.4%, an aldol condensate of acetaldehyde at 0.2% and the reaction yield from formamide to N-(α-hydroxyethyl)formamide was 97.0%.

(Conditions for liquid chromatography analysis)
Column: MCI-GEL-ODS 1HU (4.6 mm φ×250 mm).
Flow rate: 1 mL/min.
Eluent: 0.01 M $NaH_2PO_3 \cdot 2H_2O$.
Sample injection amount: 20 μL of sample diluted 1000 times with eluent.

<Production of N-(α-alkoxyethyl)formamide>

The solid component mixture containing N-(α-hydroxyethyl)formamide in the alkoxylation reaction tank 50 was mixed with 203.1 kg of methanol as an alcohol.

Subsequently, the mixed solution was kept at 5° C. and 2.05 kg of 98% sulfuric acid as an acid catalyst was added to the mixed solution. The addition was completed within 60 minutes from the start of addition. Incidentally, the temperature of the mixed solution immediately before the addition of the acid catalyst is abbreviated as "temperature Y" in the table.

The time (abbreviated as "time Z" in the table) from the addition of methanol to the solid component mixture to the start of the addition of sulfuric acid was 1 hour.

Thereafter, the temperature of the mixed solution to which sulfuric acid was added was increased to 15° C. and the mixed solution was stirred for 1 hour.

Subsequently, a 25% aqueous solution of sodium hydroxide was added to the reaction mixture after completion of the alkoxylation step until the pH reached 7, thereby neutralizing the acid catalyst.

Thereafter, potassium sulfate (inorganic salt) which was a reaction product of potassium hydrogencarbonate with sulfuric acid was subjected to solid-liquid separation by using a metal filter type pressure filter made of SUS304 (Type AAF-5734 manufactured by FUJI FILTER MFG. CO., LTD.) as the filter 60. Separability in the solid-liquid separation was favorable, and the separation was completed in 30 minutes.

The solution which was obtained by solid-liquid separation and contained a N-(α-alkoxyethyl)formamide was analyzed by liquid chromatography under the above conditions, and as a result, the solution contained N-(α-methoxyethyl)formamide (abbreviated as "MEF" in the table) at 44.7%, formamide (abbreviated as "FAM" in the table) at 0.17%, and N-(α-hydroxyethyl)formamide (abbreviated as "HEF" in the table) at 1.04%. At this time, the conversion (abbreviated as "FAM conversion" in the table) of formamide was 99.2% and the selectivity (abbreviated as "MEF selectivity" in the table) from formamide to N-(α-methoxyethyl)formamide was 97.4%. From the above, the total reaction yield (abbreviated as "total reaction yield" in the table) from formamide to N-(α-methoxyethyl)formamide was 96.6%.

These results are presented in Table 1.

Example A2

N-(α-hydroxyethyl)formamide was produced in the same manner as in Example A1.

N-(α-methoxyethyl)formamide was produced in the same manner as in Example A1 except that the temperature of the mixed solution until sulfuric acid was added thereto was changed to 30° C. in the production of N-(α-methoxyethyl)formamide.

The results are presented in Table 1.

Example A3

N-(α-hydroxyethyl)formamide was produced in the same manner as in Example A1.

N-(α-methoxyethyl)formamide was produced in the same manner as in Example A1 except that the temperature of the mixed solution until sulfuric acid was added thereto was changed to 30° C. and the time from the completion of the addition of methanol to the solid component mixture to the start of the addition of sulfuric acid was changed to 3 hours in the production of N-(α-methoxyethyl)formamide.

The results are presented in Table 1.

Comparative Example A1

N-(α-hydroxyethyl)formamide was produced in the same manner as in Example A1.

N-(α-methoxyethyl)formamide was produced in the same manner as in Example A1 except that the temperature of the mixed solution until sulfuric acid was added thereto was changed to 30° C. and the time from the completion of the addition of methanol to the solid component mixture to the start of the addition of sulfuric acid was changed to 6 hours in the production of N-(α-methoxyethyl)formamide.

The results are presented in Table 1.

Comparative Example A2

N-(α-hydroxyethyl)formamide was produced in the same manner as in Example A1.

N-(α-methoxyethyl)formamide was produced in the same manner as in Example A1 except that the temperature of the mixed solution until sulfuric acid was added thereto was changed to 25° C. and the time from the completion of the addition of methanol to the solid component mixture to the start of the addition of sulfuric acid was changed to 21 hours in the production of N-(α-methoxyethyl)formamide.

The results are presented in Table 1.

Comparative Example A3

N-(α-hydroxyethyl)formamide was produced in the same manner as in Example A1.

N-(α-methoxyethyl)formamide was produced in the same manner as in Example A1 except that the temperature of the mixed solution until sulfuric acid was added thereto was changed to 30° C. and the time from the completion of the addition of methanol to the solid component mixture to the start of the addition of sulfuric acid was changed to 21 hours in the production of N-(α-methoxyethyl)formamide.

The results are presented in Table 1.

mixed with 203.1 kg of methanol as an alcohol and 2.05 kg of 98% sulfuric acid as an acid catalyst was added thereto. The time from the completion of the addition of methanol to the solid component mixture to the start of the addition of sulfuric acid was 1 hour.

Subsequently, degassing of carbon dioxide was conducted by supplying nitrogen as an inert gas (blowing of inert gas, at linear velocity: 3.9 m/hr, pH: 1.8, and 15° C. for 110 minutes) from the lower part of the alkoxylation reaction tank 50, then supply of nitrogen was stopped, and the mixed solution was further stirred at 15° C. for 1 hour. Incidentally, the linear velocity of nitrogen in the supply of nitrogen was calculated from the inner cross-sectional area of the alkoxylation reaction tank 50, 2.82 $m^2$ and the amount of nitrogen supplied per unit time measured by using a float type nitrogen flowmeter, 11 $m^3$/hr.

Subsequently, a 25% aqueous solution of sodium hydroxide was added to the reaction mixture after completion of the alkoxylation step until the pH reached 7, thereby neutralizing the acid catalyst.

Thereafter, potassium sulfate (inorganic salt) which was a reaction product of potassium hydrogencarbonate with sulfuric acid was subjected to solid-liquid separation by using a metal filter type pressure filter made of SUS304 (Type AAF-5734 manufactured by FUJI FILTER MFG. CO., LTD.) as the filter 60. Separability in the solid-liquid separation was favorable, and the separation was completed in 30 minutes.

TABLE 1

| | | Example A1 | Example A2 | Example A3 | Comparative Example A1 | Comparative Example A2 | Comparative Example A3 |
|---|---|---|---|---|---|---|---|
| Time Z | | 1 hour | 1 hour | 3 hours | 6 hours | 21 hours | 21 hours |
| Temperature Y | | 5° C. | 30° C. | 30° C. | 30° C. | 25° C. | 30° C. |
| FAM | % by mass | 0.17 | 0.17 | 0.18 | 0.18 | 0.19 | 0.20 |
| HEF | % by mass | 1.04 | 1.04 | 1.02 | 1.02 | 1.09 | 1.14 |
| MEF | % by mass | 44.7 | 44.0 | 43.8 | 43.8 | 42.5 | 39.1 |
| FAM conversion | % | 99.2 | 97.9 | 98.2 | 97.2 | 94.2 | 92.3 |
| MEF selectivity | % | 97.4 | 97.1 | 96.4 | 95.4 | 92.4 | 89.5 |
| Total reaction yield | % | 96.6 | 95.0 | 94.6 | 92.7 | 87.0 | 82.6 |

As is apparent from the results in Table 1, it was possible to produce a N-(α-alkoxyethyl)formamide at a high total reaction yield in the respective Examples in which an acid catalyst was added to a mixed solution containing N-(α-hydroxyethyl)formamide and an alcohol within 3 hours after the alcohol was added to N-(α-hydroxyethyl)formamide. The total reaction yield was higher particularly in the case of Example 1 in which the temperature of the mixed solution was kept at 5° C. until the acid catalyst was added thereto.

On the other hand, the respective Comparative Examples in which the time until an acid catalyst was added to the mixed solution containing N-(α-hydroxyethyl)formamide and an alcohol was longer than 3 hours after the alcohol was added to N-(α-hydroxyethyl)formamide were inferior to the respective Examples in the total reaction yield.

Example B1

<Production of N-(α-hydroxyethyl)formamide>

N-(α-hydroxyethyl)formamide was produced in the same manner as in Example A1.

<Production of N-(α-methoxyethyl)formamide>

The solid component mixture containing N-(α-hydroxyethyl)formamide in the alkoxylation reaction tank 50 was Incidentally, the time required for solid-liquid separation is abbreviated as "solid-liquid separation time" in the table.

The results are presented in Table 2.

The solution which was obtained by solid-liquid separation and contained a N-(α-alkoxyethyl)formamide was analyzed by liquid chromatography under the above conditions, and as a result, the solution contained N-(α-methoxyethyl)formamide at 45.5%, formamide at 0.30%, and N-(α-hydroxyethyl)formamide at 0.80% %. At this time, the conversion of formamide was 98.5% and the selectivity from formamide to N-(α-methoxyethyl)formamide was 98.0%. From the above, the total reaction yield from formamide to N-(α-methoxyethyl)formamide was 96.6%.

The results are presented in Table 2.

In addition, the solution which was obtained by solid-liquid separation and contained a N-(α-alkoxyethyl)formamide was subjected to the analysis of carbonate by a titration method but a carbonate ion was not detected.

Incidentally, the concentration of a carbonate contained in the N-(α-alkoxyethyl)formamide obtained is abbreviated as "carbonate ion concentration in MEF" in the table.

The results are presented in Table 2.

Example B2

N-(α-hydroxyethyl)formamide was produced in the same manner as in Example A1.

N-(α-methoxyethyl)formamide was produced in the same manner as in Example B1 except that the linear velocity in the supply of nitrogen was set to 2.1 m/hr in the production of N-(α-methoxyethyl)formamide. Incidentally, the linear velocity of nitrogen in the supply of nitrogen was calculated from the inner cross-sectional area of the alkoxylation reaction tank 50, 2.82 m² and the amount of nitrogen supplied per unit time measured by using a float type nitrogen flowmeter, 6 m³/hr.

Separability in the solid-liquid separation was favorable, and the separation was completed in 30 minutes. In addition, the solution which was obtained by solid-liquid separation and contained a N-(α-alkoxyethyl)formamide was subjected to the analysis of carbonate by a titration method but a carbonate ion was not detected.

The results are presented in Table 2.

Example B3

N-(α-hydroxyethyl)formamide was produced in the same manner as in Example A1.

N-(α-methoxyethyl)formamide was produced in the same manner as in Example B1 except that the linear velocity in the supply of nitrogen was set to 1.1 m/hr in the production of N-(α-methoxyethyl)formamide. Incidentally, the linear velocity of nitrogen in the supply of nitrogen was calculated from the inner cross-sectional area of the alkoxylation reaction tank 50, 2.82 m² and the amount of nitrogen supplied per unit time measured by using a float type nitrogen flowmeter, 3 m³/hr.

Separability in the solid-liquid separation was favorable, and the separation was completed in 60 minutes. In addition, the solution which was obtained by solid-liquid separation and contained a N-(α-alkoxyethyl)formamide was subjected to the analysis of carbonate by a titration method and 280 ppm of carbonate ion was detected.

The results are presented in Table 2.

Comparative Example B1

N-(α-hydroxyethyl)formamide was produced in the same manner as in Example A1.

N-(α-methoxyethyl)formamide was produced in the same manner as in Example B1 except that nitrogen was not supplied, that is, degassing of carbon dioxide was not conducted in the production of N-(α-methoxyethyl)formamide. Separability in the solid-liquid separation was significantly poor, and it took 300 minutes to complete the separation. In addition, the solution which was obtained by solid-liquid separation and contained a N-(α-alkoxyethyl) formamide was subjected to the analysis of carbonate by a titration method and 620 ppm of carbonate ion was detected.

The results are presented in Table 2.

TABLE 2

|  |  |  | Example B1 | Example B2 | Example B3 | Comparative Example B1 |
|---|---|---|---|---|---|---|
| Conditions for inert gas supply | Temperature | ° C. | 15 | 15 | 15 | — |
|  | Time | minutes | 110 | 110 | 110 | — |
|  | Flow rate | m³/hr | 11 | 6 | 3 | — |
|  | Linear velocity | m/hr | 3.9 | 2.1 | 1.1 | — |
| FAM |  | % by mass | 0.3 | 0.3 | 0.3 | 0.3 |
| HEF |  | % by mass | 0.8 | 0.8 | 0.8 | 0.9 |
| MEF |  | % by mass | 45.5 | 45.5 | 43.6 | 44.5 |
| FAM conversion |  | % | 98.5 | 97.9 | 98.5 | 98.5 |
| MEF selectivity |  | % | 98.0 | 98.0 | 97.9 | 97.7 |
| Total reaction yield |  | % | 96.6 | 96.0 | 96.4 | 96.3 |
| Carbonate ion concentration in MEF |  | ppm | 0 | 0 | 280 | 620 |
| Time for solid-liquid separation |  | minutes | 30 | 30 | 60 | 300 |

As is apparent from the results in Table 2, the concentration of carbonate ion in the solution which was obtained by solid-liquid separation and contained a N-(α-alkoxyethyl) formamide was 500 ppm or less in the respective Examples in which degassing of carbon dioxide was conducted.

On the other hand, in Comparative Example B1 in which degassing of carbon dioxide was not conducted, separability in the solid-liquid separation after neutralization of the acid catalyst was poor, and it took a long time of 300 minutes to complete the separation in Comparative Example B1 while the separation was completed in 30 minutes in Example B1.

In addition, in Comparative Example B2 in which degassing of carbon dioxide was not conducted, the concentration of carbonate ion in the solution which was obtained by solid-liquid separation and contained a N-(α-alkoxyethyl) formamide was 620 ppm and the solution contained a carbonate at a higher concentration as compared with those in the respective Examples. For this reason, there is concern about an increase in the column bottom liquid viscosity in a case in which the solution which was obtained by solid-liquid separation in Comparative Example B1 and contained a N-(α-alkoxyethyl)formamide was purified through distillation.

INDUSTRIAL APPLICABILITY

According to the method for producing a N-(α-alkoxyethyl)formamide of the invention, it is possible to produce a N-(α-alkoxyethyl)formamide at a high yield without additional investment in plant and equipment while suppressing an increase in the temperature of a mixed solution and preventing corrosion of a pipe.

In addition, according to some aspects of the method for producing a N-(α-alkoxyethyl)formamide of the invention, it is possible to produce a N-(α-alkoxyethyl)formamide having a decreased carbonate concentration.

EXPLANATIONS OF LETTERS OR NUMERALS

1 PRODUCTION APPARATUS
20 CATALYST DISSOLVING TANK
21 FIRST SUPPLY PIPE
40 HYDROXYLATION REACTION TANK
41 SECOND SUPPLY PIPE
42 STIRRER
50 ALKOXYLATION REACTION TANK

51 THIRD SUPPLY PIPE
52 STIRRER
60 FILTER

The invention claimed is:

1. A method for producing N-(α-alkoxyethyl)formamide, comprising:

production of N-(α-hydroxyethyl)formamide by mixing formamide with acetaldehyde in presence of a carbonate and precipitating N-(α-hydroxyethyl)formamide; and production of the N-(α-alkoxyethyl)formamide by first mixing the N-(α-hydroxyethyl)formamide with an alcohol to form a mixed liquid, then adding an acid catalyst to the mixed liquid containing the N-(α-hydroxyethyl)formamide and the alcohol within 3 hours from when the mixing of the N-(α-hydroxyethyl)formamide with the alcohol is started in the production of the N-(α-alkoxyethyl)formamide, wherein carbon dioxide in a reaction liquid is degassed in the production of the N-(α-alkoxyethyl)formamide when the reaction liquid is under an acidic condition.

2. The method for producing N-(α-alkoxyethyl)formamide according to claim 1, wherein the acid catalyst is added to the mixed liquid containing the N-(α-hydroxyethyl)formamide and the alcohol after 1 minute or more and within 3 hours from when the mixing of the N-(α-hydroxyethyl)formamide with the alcohol is started in the production of the N-(α-alkoxyethyl)formamide.

3. The method for producing N-(α-alkoxyethyl)formamide according to claim 1, wherein a temperature of the mixed liquid containing the N-(α-hydroxyethyl)formamide and the alcohol immediately before addition of the acid catalyst is 30° C. or less.

4. The method for producing N-(α-alkoxyethyl)formamide according to claim 3, wherein a temperature of the mixed liquid containing the N-(α-hydroxyethyl)formamide and the alcohol immediately before addition of the acid catalyst is 10° C. or less.

5. The method for producing N-(α-alkoxyethyl)formamide according to claim 1, wherein a carbonate ion concentration in a solution that is obtained by neutralizing a reaction mixture obtained in the production of the N-(α-alkoxyethyl)formamide with a base and subjecting the reaction mixture neutralized to solid-liquid separation and contains the N-(α-alkoxyethyl)formamide is 500 ppm or less.

6. The method for producing N-(α-alkoxyethyl)formamide according to claim 1, wherein the degassing of carbon dioxide is conducted by blowing of an inert gas into the reaction liquid.

7. The method for producing N-(α-alkoxyethyl)formamide according to claim 6, wherein a linear velocity of the inert gas in the blowing of an inert gas is from 0.1 to 20 m/hr.

* * * * *